United States Patent [19]

Joentgen et al.

[11] Patent Number: 5,059,716

[45] Date of Patent: Oct. 22, 1991

[54] PROCESS FOR THE PREPARATION OF ALDEHYDES

[75] Inventors: Winfried Joentgen, Cologne; Helmut Fiege, Leverkusen, both of Fed. Rep. of Germany

[73] Assignee: Bayer Aktiengesellschaft, Leverkusen, Fed. Rep. of Germany

[21] Appl. No.: 564,226

[22] Filed: Aug. 8, 1990

[30] Foreign Application Priority Data

Aug. 23, 1989 [DE] Fed. Rep. of Germany ....... 3927786

[51] Int. Cl.$^5$ .............................................. C07C 45/41
[52] U.S. Cl. ................................... 568/435; 568/426; 568/437; 568/484; 568/490
[58] Field of Search ............... 568/484, 435, 484, 426, 568/425, 437, 490

[56] References Cited

U.S. PATENT DOCUMENTS

| | | | |
|---|---|---|---|
| 3,994,936 | 11/1976 | Andrews et al. | 568/485 |
| 4,613,700 | 9/1986 | Maki et al. | 568/435 |

FOREIGN PATENT DOCUMENTS

| | | | |
|---|---|---|---|
| 0041672 | 12/1981 | European Pat. Off. | 568/435 |
| 0300861 | 1/1989 | European Pat. Off. | 568/435 |
| 0304853 | 3/1989 | European Pat. Off. | 568/435 |

*Primary Examiner*—Werren B. Lone
*Attorney, Agent, or Firm*—Sprung Horn Kramer & Woods

[57] ABSTRACT

Aromatic and aliphatic aldehydes can be prepared from the corresponding aromatic or aliphatic carboxylic acids or the esters, anhydrides or halides thereof at elevated temperature by catalytic gas phase hydrogenation using hydrogen if use is made of a catalyst system composed of oxides of titanium and/or vanadium and of one or more co-metals, the co-metals being selected from the group consisting of chromium, molybdenum, cobalt, nickel, zinc, cadmium and copper.

17 Claims, No Drawings

PROCESS FOR THE PREPARATION OF ALDEHYDES

BACKGROUND OF THE INVENTION

1. Field of the Invention

The present invention relates to a process for the preparation of aromatic and aliphatic aldehydes by catalytic gas phase hydrogenation of aromatic or aliphatic carboxylic acids or of some of their derivatives using a catalyst system based on titanium dioxide and/or vanadium oxide.

2. Description of the Related Art

It is known that aromatic and aliphatic carboxylic acids or carboxylic esters can be reduced by molecular hydrogen using various catalysts to give the corresponding aldehydes. For instance, U.S. Pat. No. 3,935,265 discloses that alkyl esters of aromatic carboxylic acids can be reduced by hydrogen at 400°-600° C. on $Al_2O_3$; for example, methyl benzoate is converted to benzaldehyde with a selectivity of 37%, the conversion of the ester being 39%. Furthermore, it is known that zirconium dioxide alone (U.S. Pat. No. 4,328,373) or in combination with the oxides of other metals such as chromium, manganese, iron, zinc, cobalt, bismuth, lead, rhenium or main group III elements such as boron, aluminum, gallium, indium or thallium (EP 150,961) or together with oxides of elements of the lanthanide group (U.S. Pat. No. 4,328,373) is capable of reducing carboxylic acids or the esters thereof with hydrogen to the corresponding aldehydes. The abovementioned U.S. Pat. No. 4,328,373 furthermore discloses that, like zirconium dioxide, the oxides of yttrium, cerium, praseo-dymium, thorium and uranium are also effective, these like zirconium dioxide also being useable in combination with aluminum oxide.

U.S. Pat. No. 4,585,899 discloses that manganese dioxide in combination with aluminum oxide and silicon dioxide is also effective. EP 290,096 discloses that manganese dioxide can be deposited on various carriers such as aluminum oxide, zirconium dioxide, titanium dioxide, cerium(III) oxide, hafnium dioxide or niobium(V) oxide. No specific action of the carriers in combination with the manganese dioxide is mentioned in the above publication. According to EP 290,096, the type of preparation of the manganese oxide is crucial for the activity of the catalyst.

The effectiveness of a manganese dioxide/titanium dioxide combination is not described in EP 290,096. The present applicant's own experiments showed that a catalyst consisting of, for example, 23% by weight of manganese dioxide on titanium dioxide and prepared by coprecipitation of the components was not especially effective at 370° C. for the abovementioned purpose. At higher temperatures, in particular above 400° C., although the activity of the conversion of carboxylic acids or the derivatives thereof increased, the selectivity of conversion to the desired aldehydes declined to an industrially unacceptable level.

SUMMARY OF THE INVENTION

Surprisingly, it has now been found that catalyst systems composed of titanium dioxide and/or vanadium oxide and one or more oxides of specific co-metals give the desired aldehydes at high conversion rates and with high selectivity.

The present invention accordingly provides a process for the preparation of aromatic and aliphatic aldehydes by catalytic gas phase hydrogenation of the corresponding aromatic or aliphatic carboxylic acids or the esters, anhydrides or halides thereof at elevated temperature using hydrogen, characterized in that a catalyst system composed of oxides of titanium and/or vanadium, whereby at least one part of the vanadium is present in the oxidation stage IV, and of one or more co-metals is used, the co-metals being selected from the group consisting of chromium, molybdenum, cobalt, nickel, zinc, cadmium and copper.

DETAILED DESCRIPTION OF THE INVENTION

Preference is given to selection of the co-metal(s) from the group consisting of chromium, molybdenum, nickel, zinc, cadmium and copper and particular preference is given to selection from the group consisting of chromium, molybdenum, zinc, cadmium and copper. In many cases favourable results have been achieved in particular using the titanium dioxide/chromium(III) oxide or vanadium(IV) oxide/chromium(III) oxide combination.

The catalyst system which is to be used according to the invention contains 1 to 25 g-equivalents, preferably 3 to 12 g-equivalents, of the desired co-metal(s), relative to 100 g-equivalents of all metals present.

Although in addition to the titanium dioxide and/or vanadium oxide, oxides of two or more co-metals may be present in the catalyst system which is to be used according to the invention, it is preferable to use ony the oxide of one co-metal.

The catalyst systems to be used according to the invention can be prepared from readily accessible materials by simple processes. The use of costly starting materials such as zirconium dioxide or rare earth oxides is avoided. However, these catalyst systems which are to be used according to the invention in some case give the desired aldehydes at even higher activities with regard to the conversion rate than the catalyst systems known from the literature, the selectivities being similar.

The preparation of the catalyst systems which are to be used according to the invention can be carried out, for example, by impregnating titanium dioxide with a suitable metal salt solution of one or more co-metals or by co-precipitation of the metal components, followed in either case by drying and calcination.

In the former case previously prepared pellets of titanium dioxide can be impregnated by repeated spraying or soaking with a solution of salts of one or more co-metals, these salts being decomposable at elevated temperature. The impregnated pellets are dried and calcinated at 400° to 800° C., preferably at 500° to 750° C.

In the latter case, a water-soluble titanium salt and one or more metal salts of the co-metal(s) can be precipitated, for example, at a pH of 7 to 9 using aqueous ammonia or sodium hydroxide or another suitable basic precipitating agent. The precipitated hydroxides are then washed and dried, for example, for 24 hours at 100° to 150° C., optionally in vacuo, and are then calcinated, likewise at 400° to 800° C., preferably at 500° to 750° C. A suitable calcination period is 4 to 8 hours. In a variant of this method of preparation, titanium tetrachloride is added to a cooled metal salt solution of the co-metal(s). The subsequent processing (precipitation, drying and calcination) is carried out in the manner already described.

The catalyst system obtained after calcination can be used directly after comminution to the desired particle size. However, the very finely ground catalyst system may also be pressed into pellets; this can be carried out using a pelletizing auxiliary to improve the slip properties (for example, graphite).

Among the preparation variants which have been described, that using titanium tetrachloride has proved particularly advantageous.

The preparation of the catalyst system to be inventively employed on the basis of vanadium oxide can also be carried out according to the preparation methods as described in detail above. Instead of the titanium component, however, the respective vanadinium compound is used. As vanadinium compound, vanadinium (IV) oxide, a mixture of vanadinium (III) and vanadinium (IV) oxide or water-soluble vanadinium (IV) compounds, e.g. vanadyl sulphate or vanadyl oxalate, can be employed. A preparation variant with the use of vanadyl sulphate which is accessible by reduction of vanadinium (V) oxide with sulphur dioxide or with the use of vanadyl oxalate which is accessible by the respective reduction with oxlic acid, has proved especially advantageous.

After putting together the vanadyl compound and one or more water-soluble salt(s) of one or more co-metal(s), the metals are precipitated as hydroxides at pH 7 to 9. The hydroxides are washed, dried and calcined at 350°–700° C., preferably at 400°–600° C.

The catalyst system which is to be used according to the invention enables a large number of aromatic and aliphatic carboxylic acids, carboxylic esters, carboxylic acid anhydrides and carboxylic acid halides to be converted into the corresponding aldehydes. The aliphatic carboxylic acids or their derivatives include the araliphatic and cycloaliphatic carboxylic acids and their derivatives.

Aromatic and aliphatic carboxylic acids and derivatives include, in particular, those of the formulae

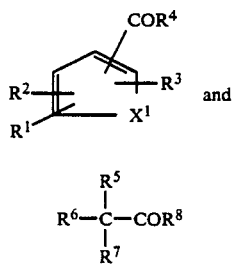

in which $R^1$ is hydrogen, straight-chain or branched $C_1$–$C_8$-alkyl, straight-chain or branched $C_1$–$C_8$-alkoxy, $R^3$-substituted phenyl, naphthyl, $R^3$-substituted phenoxy, $R^3$-substituted benzyl, $R^3$-substituted benzyloxy, hydroxyl, amino, NH-($C_1$–$C_8$-alkyl), N-($C_1$–$C_8$-alkyl)$_2$, halogen or $COR^4$, $R^2$ represents hydrogen, straight-chain or branched $C_1$–$C_8$-alkyl, straight-chain or branched $C_1$–$C_8$-alkoxy, or $R^3$-substituted phenyl, where $R^1$ and $R^2$ may together form a condensed benzene ring which may be substituted by hydroxyl, amino, methyl, ethyl, methoxy or ethoxy, $R^3$ may be hydrogen, straight-chain or branched $C_1$–$C_8$-alkyl, straight-chain or branched $C_1$–$C_8$-alkoxy, hydroxyl, amino or halogen, $R^4$ is hydroxyl, $C_1$–$C_4$-alkoxy, chlorine, bromine or

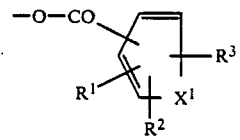

where in the latter case (anhydride formation), $R^1$ does not assume the meaning $COR^4$, $X^1$ represents —O—, —N—, —S—, —N=CH— or —CH=CH—, $R^5$ is hydrogen or straight-chain or branched $C_1$–$C_8$-alkyl, $R^6$ represents straight-chain or branched $C_1$–$C_8$-alkyl, $R^3$-substituted phenyl or halogen, $R^7$ represents straight-chain or branched $C_1$–$C_8$-alkyl or $R^3$-substituted phenyl, where the $C_1$–$C_8$-alkyl may be substituted by halogen, methoxy or ethoxy and where furthermore $R^6$ and $R^7$ are together dimethylene, tetramethylene or pentamethylene, and $R^8$ is hydroxyl, $C_1$–$C_4$-alkoxy, chlorine, bromine or the group —O—CO—C($R^5,R^6,R^7$).

Examples of straight-chain or branched $C_1$–$C_8$-alkyl are methyl, ethyl, propyl, isopropyl, butyl, isobutyl, tert-butyl and the isomeric pentyls, hexyls or octyls. Preference is given to the abovementioned $C_1$–$C_4$-alkyl radicals, particular preference being given to methyl or ethyl.

Examples of straight-chain or branched $C_1$–$C_8$-alkoxy are methoxy, ethoxy, propoxy, isopropoxy, butoxy, isobutoxy, tert-butoxy and the isomeric pentyloxy, hexyloxy and octyloxy. Preference is given to alkoxy having 1 to 4 carbon atoms and particular preference is given to methoxy or ethoxy.

Examples of suitable halogens are fluorine, chlorine, bromine, preferably fluorine or chlorine.

$R^1$ and $R^2$ may together form a condensed benzene ring, so that the aromatic carboxylic acid or its derivative are derived from the naphthalene, quinoline, isoquinoline, indole, coumarone or thionaphthene system.

Suitable carboxylic acids or derivatives thereof are the carboxylic acids themselves, their esters with a $C_1$–$C_4$-alcohol, their chlorides, bromides or their anhydrides.

If $R^1$ is the radical $COR^4$, this defines a dicarboxylic acid or its derivative, from which the corresponding dialdehyde is obtained.

The straight-chain or branched $C_1$–$C_8$-alkyl may, in particular in aliphatic carboxylic acids or derivatives thereof, be substituted by halogen such as fluorine, chlorine, bromine, preferably fluorine or chlorine, by methoxy or ethoxy.

If, in the case of the aliphatic carboxylic acids or derivatives, one or more radicals are phenyl, this defines one of the class of araliphatic carboxylic acids.

Furthermore, $R^6$ and $R^7$ may together denote dimethylene, tetramethylene or pentamethylene, thus defining one of the class of cycloaliphatic carboxylic acids having a 3-, 5- or 6-membered ring. Preferably, $R^6$ and $R^7$ may together denote tetramethylene or pentamethylene.

Among the aromatic carboxylic acids and derivatives, preference is given to those of the formula

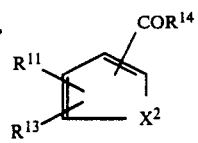
(III)

in which $R^{11}$ is hydrogen, straight-chain or branched $C_1$–$C_8$-alkyl, straight-chain or branched $C_1$–$C_8$-alkoxy, $R^{13}$-substituted phenyl, $R^{13}$-substituted phenoxy, hydroxyl, amino, NH-($C_1$–$C_8$-alkyl), N-($C_1$–$C_8$-alkyl)$_2$ or halogen, $R^{13}$ represents hydrogen, straight-chain or branched $C_1$–$C_8$-alkyl, straight-chain or branched $C_1$–$C_8$-alkoxy, hydroxyl or halogen, $R^{14}$ is hydroxyl, methoxy, ethoxy or chlorine, and $X^2$ represents —CH=CH— or —N=CH—, preferably —CH=CH—.

Among the aromatic carboxylic acids or derivatives thereof, particular preference is given to those of the formula

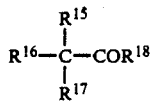
(IV)

in which $R^{21}$ is hydrogen, straight-chain or branched $C_1$–$C_4$-alkyl, straight-chain or branched $C_1$–$C_4$-alkoxy, $R^{23}$-substituted phenyl, $R^{23}$-substituted phenoxy, hydroxyl, amino, methylamino, ethylamino, dimethylamino, diethylamino, fluorine or chlorine, $R^{23}$ represents hydrogen, straight-chain or branched $C_1$–$C_4$-alkyl, straight-chain or branched $C_1$–$C_4$-alkoxy, hydroxyl, fluorine or chlorine, and $R^{14}$ has the range of meaning given above.

Among the aliphatic carboxylic acids and derivatives thereof, preference is given to those of the formula $$R^{16}-\underset{\underset{R^{17}}{|}}{\overset{\overset{R^{15}}{|}}{C}}-COR^{18} \quad (V)$$

in which $R^{15}$ represents hydrogen, methyl or ethyl, $R^{16}$ is a straight-chain or branched $C_1$–$C_8$-alkyl or phenyl, $R^{17}$ is methyl or ethyl, whereby $R^{16}$ and $R^{17}$ furthermore together can denote tetramethylene or pentamethylene, and $R^{18}$ represents hydroxyl, methoxy, ethoxy or chlorine.

Particularly preferred aromatic and aliphatic carboxylic acids and derivatives thereof are benzoic acid, methyl benzoate, tert.-butylbenzoic acid, phenoxybenzoic acid, pivalic acid, toluic acid and m-chlorobenzoic acid.

The gas phase hydrogenation is carried as a continuous operation using a temperature of 300° to 500° C., preferably 325° to 425° C., and a pressure of 0.1 to 10 bar, preferably atmospheric pressure. The hydrogenation is carried out using molecular hydrogen which can be diluted by adding an inert gas such as argon or nitrogen. Similarly, industrial hydrogen may be used. The molar ratio of carboxylic acid or its derivative to hydrogen is 1:1–500, preferably 1:5–50. If the carboxylic acid derivative used is an anhydride, this is calculated as 2 mol of the carboxylic acid.

The aromatic and aliphatic carboxylic acids or their derivatives may be introduced into an evaporator in the form of a solid, a melt, or as a solution in a suitable solvent such as toluene, benzene, cyclohexane or similar solvents known to a person skilled in the art, and are then fed in vapour form to the catalyst system which is to be used according to the invention. The feed rate of the carboxylic acid or the derivatives thereof is 0.05 to 2 h$^{-1}$ (LHSV = liquid hourly space velocity); the feed rate of the hydrogen is 170 to 3350 h$^{-1}$ (GHSV = gaseous hourly space velocity).

The aldehydes which can be prepared according to the invention can be used as fragrances or precursors for active ingredients in the plant protection field or pharmaceutical field.

EXAMPLES 1–8

Preparation of the catalysts

To an ice-cooled aqueous solution of x mol % of the co-metal salt were added dropwise y mol % of TiCl$_4$. The mixture containing hydrochloric acid was brought to a pH of 7 to 9 using aqueous ammonia (in the case of Cr, Zn, Mo, Mn) or sodium hydroxide solution or sodium carbonate solution (in the case of Cu, Cd). The precipitated hydroxides were filtered off under suction, washed and dried in vacuo at 130° C. Then they were calcinated at 700° C. (Cr, Mn, Zn, Cu) or 550° to 600° C. (Cd, Mo). After comminution to particle sizes of 8 to 18 mesh (1.00 to 2.5 mm diameter) the catalyst was used for the hydrogenation. In the case of Example 8, AlCl$_3$ was used instead of TiCl$_4$.

These catalysts were used to hydrogenate benzoic acid under the following conditions:

| Catalyst: | 25 g (8–18 mesh) |
|---|---|
| Temperature: | 350° C. |
| Duration of experiment: | 4 hours |
| Mole ratio acid/hydrogen: | 1:30 |
| Pressure: | 1 atm |
| Feed rate of acid: | 0.09 LHSV (h$^{-1}$) |
| H$_2$: | 550–620 GHSV (h$^{-1}$) |

| | Catalyst composition | | Conversion % | Aldehyde selectivity % | Space/time yield mol · kg cat.$^{-1}$ · h$^{-1}$ |
|---|---|---|---|---|---|
| Example | y mol % TiO$_2$ | x mol % Me | | | |
| 1 | 90 | 10 (Cr) | 79 | 95 | 0.602 |
| 2 | 95 | 5 (Cd) | 91 | 86 | 0.627 |
| 3 | 90 | 10 (Zn) | 23 | 92 | 0.170 |
| 4 | 95 | 5 (Mo) | 81 | 48 | 0.310 |
| 5 | 95 | 5 (Cu) | 72 | 56 | 0.320 |
| 6* | 95 | 5 (Mn) | 1.5 | 42 | 0.005 |
| 7* | 80 | 20 (Mn) | 4 | 70 | 0.020 |
| 8* | 95 (Al) | 5 (Cr) | 4 | 88 | 0.027 |

*)Comparison

EXAMPLES 9 AND 10

The procedure described in Example 1 was followed (catalyst, temperature, pressure and duration of the experiment), but other starting materials were used.

| Acid derivative | LHSV | GHSV | Conversion % | Aldehyde selectivity % | Space/time yield mol · kg cat.$^{-1}$ · h$^{-1}$ |
|---|---|---|---|---|---|
| 9 Methyl benzoate | 0.11 | 590 | 86 | 82 | 0.620 |
| 10 Benzoyl chloride | 0.10 | 580 | 82 | 45 | 0.320 |

EXAMPLE 11

Example 1 was repeated, but at 370° C. The duration of the experiment was extended to 18 h.

| Carboxyl component | LHSV | GHSV | Conversion % | Aldehyde selectivity % | Space/time yield mol · kg cat.$^{-1}$ · h$^{-1}$ |
|---|---|---|---|---|---|
| Benzoic acid | 0.17 | 1000 | 84 | 95 | 1.2 |

EXAMPLES 12–18

These examples were carried out at 370° C. for a duration of 4 h using a $TiO_2$ (92.5%)/$Cr_2O_3$ (7.5%) catalyst.

EXAMPLES 19–21

These examples were carried out at 370° C. for a duration of 4 h using a $TiO_2$ (95%)/CdO (5%) catalyst.

| Exp. | Carboxyl component | LHSV | GHSV | Conversion % | Aldehyde selectivity % | Space-time yield mol · kg cat$^{-1}$ · h$^{-1}$ |
|---|---|---|---|---|---|---|
| 12 | p-tert-butyl-benzoic acid | 0.15 | 700 | 68 | 90 | 0.550 |
| 13 | o-methylbenzoic acid | 0.13 | 700 | 52 | 90 | 0.480 |
| 14 | trimethylacetic acid | 0.14 | 700 | 72 | 86 | 0.770 |
| 15 | m-phenoxybenzoic acid | 0.16 | 700 | 78 | 85 | 0.550 |
| 16 | m-chlorobenzoic acid | 0.08 | 350 | 70 | 56 | 0.260 |
| 17 | p-methoxybenzoic acid | 0.17 | 700 | 58 | 84 | 0.630 |
| 18 | cyclohexane-carboxylic acid | 0.17 | 700 | 70 | 88 | 0.840 |
| 19 | p-tert-butyl-benzoic acid | 0.15 | 350 | 97 | 40 | 0.310 |
| 20 | o-methylbenzoic acid | 0.16 | 350 | 79 | 46 | 0.460 |
| 21 | trimethylacetic acid | 0.14 | 350 | 84 | 66 | 0.680 |

EXAMPLE 22

Preparation of a $VO_2/Cr_2O_3$ catalyst

Y/2 moles of vanadium pentoxide were suspended in a 20% strength aqueous $H_2SO_4$. The suspension was reduced with gaseous sulphur dioxide while boiling. The vanadyl sulphate solution was mixed with x moles of a chromium salt in water and subsequent precipitated with aqueous $NH_3$ at pH 7–9. The precipitated hydroxides were filtrated and washed free of salts. The residue was dried 12 h in vacuo at 110° C. and at last calcined 6 h under inert gas at 450° C. One obtained a catalyst which contained y g-equivalents vanadium and x g-equivalents chromium; for the following example y=80 and x=20 were adjusted.

EXAMPLE 23

Hydrogenation of benzoic acid:

| Catalyst | $VO_2/Cr_2O_3$ (80/20) |
|---|---|
| Substrate | bezoic acid |
| Temperature | 380° C. |
| Pressure | 1.013 bar |
| Duration | 30 h |
| Feed rate of acid | 0.15 h$^{-1}$ (LHSV) |
| Feed rate of hydrogen | 800 h$^{-1}$ (GHSV) |

| Conversion | Aldehyde selectivity | Toluene selectivity | Benzene selectivity | Space-time yield |
|---|---|---|---|---|
| 56.5% | 85% | 11% | 1.5% | 0.63 mole-kg cat. $^{-1}$ · h$^{-1}$ |

What is claimed is:

1. A process for the preparation of an aromatic or an aliphatic aldehyde from aromatic carboxylic acids and derivatives of the formulae

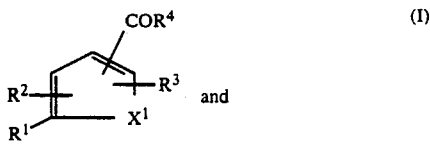 (I)

and

 (II)

in which $R^1$ is hydrogen, straight-chain or branched $C_1$–$C_8$-alkyl, straight-chain or branched $C_1$–$C_8$-alkoxy, $R^3$-substituted phenyl, naphthyl, $R^3$-substituted phenoxy, $R^3$-substituted benzyl, $R^3$-substituted benzyloxy, hydroxyl, amino, NH-($C_1$–$C_8$-alkyl), N-($C_1$–$C_8$-alkyl)$_2$, halogen or COR$^4$, $R^2$ represents hydrogen, straight-chain or branched $C_1$-$C_8$-alkyl, straight-chain or branched $C_1$-$C_8$-alkoxy, or $R^3$-substituted phenyl, where $R^1$ and $R^2$ may together form a condensed benzene ring which may be substituted by hydroxyl, amino, methyl, ethyl, methoxy or ethoxy, $R^3$ may be hydrogen, straight-chain or branched $C_1$-$C_8$-alkyl, straight-chain or branched $C_1$-$C_8$-alkoxy, hydroxyl, amino or halogen, $R^4$ is hydroxyl, $C_1$-$C_4$-alkoxy, chlorine, bromine or the group

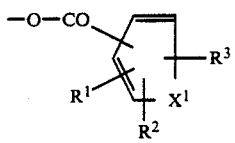

where in the latter case of anhydride formation, $R^1$ does not assume the meaning $COR^4$, $X^1$ represents —O—, —N—, —S—, —N=CH— or —CH=CH—, $R^5$ is hydrogen or straight-chain or branched $C_1$-$C_8$-alkyl, $R^6$ represents straight-chain or branched $C_1$-$C_8$-alkyl, $R^3$-substituted phenyl or halogen, $R^7$ represents straight-chain or branched $C_1$-$C_8$-alkyl or $R^3$-substituted phenyl, where the $C_1$-$C_8$-alkyl may be substituted by halogen, methoxy or ethoxy and where furthermore $R^6$ and $R^7$ are together dimethylene, tetramethylene or pentamethylene, and $R^8$ is hydroxyl, $C_1$-$C_4$-alkoxy, chlorine, bromine or the group —O—CO—C($R^5$,$R^6$, $R^7$), by catalytic gas phase hydrogenation of the corresponding aromatic or aliphatic carboxylic acid or the ester, anhydride or halide thereof at a temperature of 300° to 500° C. using hydrogen, wherein a catalyst system composed of an oxide of titanium and/or vanadium whereby at least a part of the vanadium is present in the oxidation stage IV, and of one or more co-metals is used, the co-metals being selected from the group consisting of a chromium, molybdenum, cobalt, nickel, zinc, cadmium and copper.

2. The process of claim 1, wherein the co-metal(s) is/are selected from the group consisting of chromium, molybdenum, nickel, zinc, cadmium and copper.

3. The process of claim 2, wherein the co-metal(s) is/are selected from the group consisting of chromium, molybdenum, zinc cadmium and copper.

4. The process of claim 1, wherein the catalyst system contains, in addition to the titanium or the vanadium, respectively, only one co-metal.

5. The process of claim 4, wherein the co-metal is chromium.

6. The process of claim 5, wherein the catalyst system consists of titanium oxide and chromium(III) oxide.

7. The process of claim 5, wherein the catalyst consists of vanadium(IV) oxide and chromium(III) oxide.

8. The process of claim 1, wherein the catalyst system contains 1 to 25 g-equivalents of the desired co-metal(s) per 100 g-equivalents of the sum of all metals.

9. The process of claim 8, wherein the catalyst system contains 3-12 g-equivalents of the desired co-metal(s) per 100 g-equivalents of the sum of all metals.

10. The process of claim 1, wherein the titanium containing catalyst system is prepared by the following steps:
a) addition of titanium tetrachloride to an aqueous solution of the salt or salts of one or more co-metals,
b) precipitation of the metals as the hydroxides at a pH of 7 to 9,
c) washing of the hydroxides followed by drying,
d) calcination at 400° to 800° C. 750° C.

11. The process of claim 10, wherein calcination is carried out at 500° to 750° C.

12. The process of claim 1, wherein the vanadium containing catalyst system is prepared by the following steps:
a) a reduction of vanadium pentoxide to a water-soluble vanadyl compound,
b) mixing of the vanadyl compound with one or more water-soluble salt(s) of one or more co-metals,
c) precipitation of the metals as the hydroxides at a pH of 7 to 9,
d) washing of the hydroxide followed by drying,
e) calcination at 350° to 700° C.

13. The process of claim 12, wherein calcination is carried out at 400° to 600° C.

14. The process of claim 1, wherein the aromatic carboxylic acids and derivates thereof which are used are those of the formula

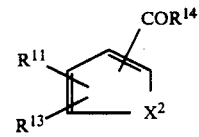

in which
$R^{11}$ is hydrogen, straight-chain or branched $C_1$-$C_8$-alkyl, straight-chain or branched $C_1$-$C_8$-alkoxy, $R^{13}$-substituted phenyl, $R^{13}$-substituted phenoxy, hydroxyl, amino, NH-($C_1$-$C_8$-alkyl), N-($C_1$-$C_8$-alkyl)$_2$ or halogen,
$R^{13}$ represents hydrogen, straight-chain or branched $C_1$-$C_8$-alkyl, straight-chain or branched $C_1$-$C_8$-alkoxy, hydroxyl or halogen,
$R^{14}$ is hydroxyl, methoxy, ethoxy or chlorine, and
$X^2$ represents —CH=CH— or —N=CH—, preferably —CH=CH—, 15. The process of claim 14, wherein $X^2$ represents —CH=CH—.

16. The process of claim 14, wherein the aromatic carboxylic acids or derivatives therof which are used are those of the formula

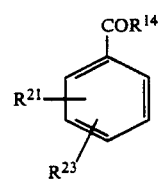

in which
$R^{21}$ is hydrogen, straight-chain or branched $C_1$-$C_4$-alkyl, straight-chain or branched $C_1$-$C_4$-alkoxy, $R^{23}$-substituted phenyl, $R^{23}$-substituted phenoxy, hydroxyl, amino, methylamino, ethylamino, dimethylamino, diethylamino, fluorine or chlorine, $R^{23}$ represents hydrogen, straight-chain or branched $C_1$–$C_4$-alkyl, straight-chain or branched $C_1$–$C_4$-alkoxy, hydroxyl, fluorine or chlorine, and $R^{14}$ is hydroxyl, methoxy, ethoxy or chlorine.

17. The process of claim 1, wherein the aliphatic carboxylic acids and derivatives thereof which are used are those of the formula

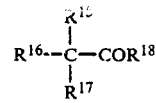

in which
$R^{15}$ represents hydrogen, methyl or ethyl,
$R^{16}$ is a straight-chain or branched $C_1$–$C_8$-alkyl or phenyl,
$R^{17}$ is methyl or ethyl, $R^{16}$ and $R^{17}$ furthermore together denoting tetramethylene or pentamethylene, and
$R^{18}$ represents hydroxyl, methoxy, ethoxy or chlorine.

* * * * *